(12) United States Patent
Dahners

(10) Patent No.: US 6,955,677 B2
(45) Date of Patent: Oct. 18, 2005

(54) MULTI-ANGULAR FASTENING APPARATUS AND METHOD FOR SURGICAL BONE SCREW/PLATE SYSTEMS

(75) Inventor: Laurence E. Dahners, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 256 days.

(21) Appl. No.: 10/271,635

(22) Filed: Oct. 15, 2002

(65) Prior Publication Data

US 2004/0073218 A1    Apr. 15, 2004

(51) Int. Cl.[7] ............................................. A61B 17/56
(52) U.S. Cl. .................................................... 606/69
(58) Field of Search .............................. 606/69, 70, 71, 606/72, 73, 60, 61, 62

(56) References Cited

U.S. PATENT DOCUMENTS

| | | | |
|---|---|---|---|
| 3,741,205 A * | 6/1973 | Markolf et al. ............... | 606/61 |
| 3,906,550 A | 9/1975 | Rostoker et al. | |
| 5,198,308 A | 3/1993 | Shetty et al. | |
| 5,607,426 A * | 3/1997 | Ralph et al. .................. | 606/61 |
| 5,709,686 A | 1/1998 | Talos et al. | |
| 5,735,853 A * | 4/1998 | Olerud ........................ | 606/71 |
| 5,797,912 A * | 8/1998 | Runciman et al. ............ | 606/69 |
| 5,954,722 A * | 9/1999 | Bono ........................... | 606/61 |
| 6,206,881 B1 | 3/2001 | Frigg et al. | |
| 6,214,049 B1 | 4/2001 | Gayer et al. | |
| 6,306,140 B1 * | 10/2001 | Siddiqui ...................... | 606/73 |
| 6,379,359 B1 | 4/2002 | Dahners | |
| 6,454,769 B2 * | 9/2002 | Wagner et al. ................ | 606/69 |

* cited by examiner

*Primary Examiner*—Pedro Philogene
(74) *Attorney, Agent, or Firm*—Jenkins, Wilson & Taylor, P.A.

(57) ABSTRACT

A fastening apparatus includes a fastener and a fastener receiving member. The apparatus enables the fastener to be affixed to the fastener receiving member at a variable insertion angle selected by the user. The fastener includes an elongate section and an adjoining head section. Both the elongate section and the head section are threaded. The fastener receiving member includes one or more apertures through which one or more corresponding fasteners can be inserted. Each aperture includes a contact region formed or disposed on an inside surface defining the aperture. The contact region includes a porous matrix of protrusions or fiber metal having a density and strength sufficient to render contact region tappable by the thread of the head section of the fastener. The thread on the head section is driven into the contact region at the selected insertion angle. As a result, the thread of the head section taps into the material of the contact region such that the fastener is affixed to the fastener receiving member and maintained at the insertion angle.

76 Claims, 9 Drawing Sheets

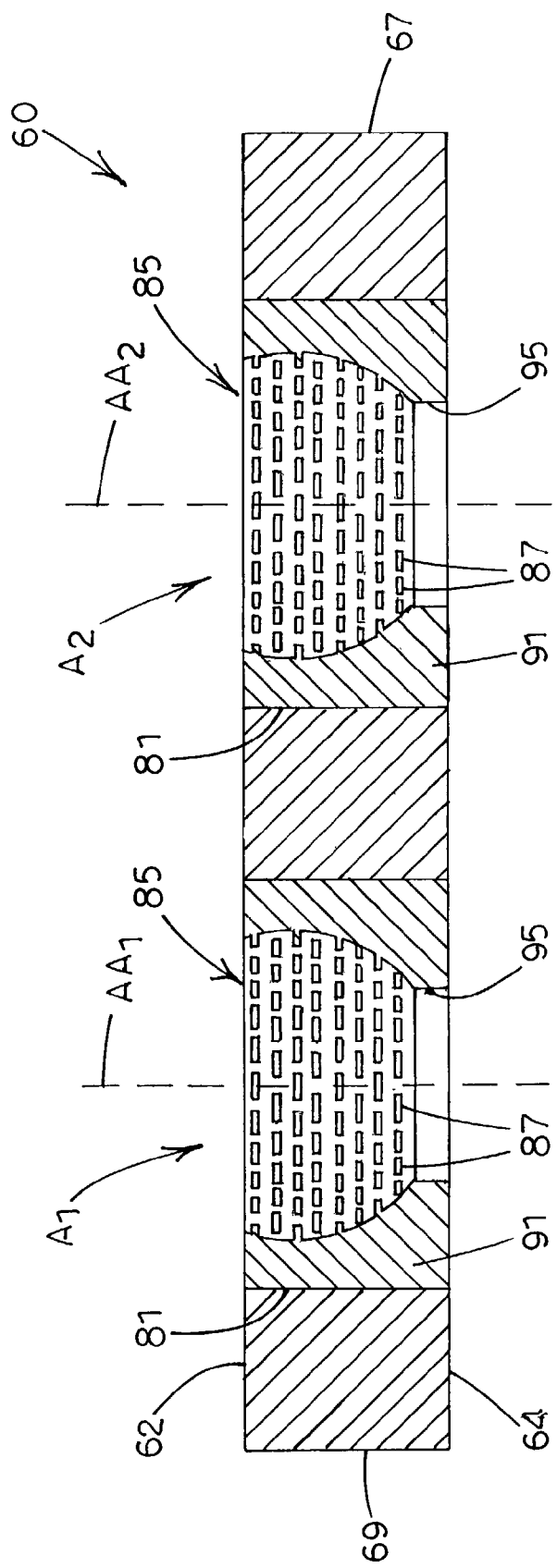

MULTI-ANGULAR FASTENING APPARATUS AND METHOD FOR SURGICAL BONE SCREW/PLATE SYSTEMS

TECHNICAL FIELD

The present invention relates generally to the design of fasteners and components to which fasteners are affixed. A specific application of the present invention relates to the design and use of bone screw/plate systems in the course of orthopaedic surgical procedures.

BACKGROUND ART

A variety of techniques exist in the field of orthopaedic surgery for treating bone fractures. Many known techniques utilize bone screws and bone fixation plates. Typically, the plate is used to stabilize the site of a bone fracture, and one or more bone screws are inserted through apertures of the plate and threaded into the bone material so as to secure the plate to the bone material. It is also known that bone screw/plate systems can be improved by machining a thread onto the head of the bone screw, in addition to the thread normally machined onto the main shaft of the screw. In connection with the use of threaded-head screws, the apertures of the plate are threaded to matingly receive the threads of the screw head. Thus, as the screw is inserted into an aperture of the plate and threaded into the bone material, the head of the screw likewise is threaded into the aperture. As a result, the screw becomes rigidly affixed to the plate, in effect locking to the plate rather than simply bearing against the plate. Examples of threaded-head bone screws and threaded-aperture bone plates are disclosed in U.S. Pat. No. 5,709,686 to Talus et al.; U.S. Pat. No. 6,206,881 to Frigg et al.; and U.S. Pat. No. 6,306,140 to Siddiqui.

The use of threaded-head screws and threaded-aperture plates provides certain advantages. It is known that some types of small bone fragments tend to change position relative to the plate over time. This deleterious condition can result from the "toggling" of the screws affixed to the plate. However, when multiple screws are rigidly fixed to the plate by mating the respective threads of the screw heads with the threads of the corresponding plate apertures, the screws do not toggle in the plate. The locking action provided by the threaded-head screw in combination with the threaded-aperture plate prevents motion between the bone fragment and the plate as well as premature loosening of the screws.

Although the use of threaded-head screws has provided improvements in orthopaedic surgical techniques, there remains the disadvantage that currently available screw/plate systems are unidirectional. That is, the thread formed on the inside surface of the aperture of the plate is structurally fixed at a constant helical angle with respect to the central axis passing through the center point of the aperture. Hence, the head of a conventional threaded-head screw can only be rigidly affixed to the plate by mating its thread with that of the aperture, such that the bone screw is always inserted and threaded in one direction, e.g., perpendicularly or coaxially with respect to the plate.

It would therefore be advantageous to provide a screw/plate system that allows the surgeon to choose the angle at which the screw is inserted through, and rigidly affixed in, an aperture of the plate. Such an improvement would enable the surgeon to direct the bone screw toward bone fragments that are not situated directly beneath the aperture of the plate, and would also provide flexibility in the placement of the plate in relation to the bone fracture. The ability to choose the angle at which the screw is threaded into the bone material would allow the surgeon to better tailor the application of the screw/plate system to the specific nature of the bone fracture suffered by the individual orthopaedic patient, and additionally allow the surgeon to adjust his or her application strategy as necessary after the surgical site has been accessed but prior to insertion of the screw into the bone material. Additionally, in situations where a screw is intended for coaxial insertion into an aperture, the improvement would allow a secure fit between the screw and aperture even if the screw is unintentionally inserted in non-coaxial relation to the aperture.

DISCLOSURE OF THE INVENTION

The present invention in broad terms provides a plate or other component suitable for affixation by a fastener. The plate has one or more apertures through which one or more corresponding fasteners can be inserted. Notably absent from these apertures are any forms of permanent internal thread structures as found in the prior art and which, as indicated above, are a limitation in applications such as the treatment of bone trauma. Each aperture is bounded by a region structured to enable the fastener, and particularly a threaded head portion of the fastener, to be tapped into the material constituting the region. By providing this tappable region, the fastener can be inserted at any desired angle in relation to the aperture, thereby providing significant flexibility in practice. While it is contemplated that the invention can be applied in a wide range of fastening and fixation techniques, particular advantage is found in the field of orthopaedic surgery. Embodiments of the invention can be practiced in any surgical procedure that conventionally involves the use of bone screw/plate systems. Examples include the treatment of general bone trauma, stabilization of metaphyseal fractures, treatment of osteoporotic bones, bone fusion, joint prosthesis, spinal alignment or correction, and the like.

According to one embodiment of the present invention, a surgical plate adapted for fixation with a bone screw is provided. The plate comprises first and second opposing major surfaces, and an inside surface extending between the first and second major surfaces. The inside surface defines an aperture that is generally coaxially disposed about an aperture axis. A non-threaded tappable contact region is disposed on the inside surface. The tappable contact region has a minimum inside diameter that is large enough to permit a bone screw to pass therethrough at an insertion angle defined between a longitudinal axis of the fastener and the aperture axis. The tappable contact region is adapted for being tapped by an external thread of the bone screw to affix the bone screw to the tappable contact region at the insertion angle.

According to one aspect of this embodiment, the tappable contact region is formed in the inside surface of the fastener receiving member. According to another aspect, the tappable contact region comprises an insert that is fitted to the inside surface.

According to a further aspect of this embodiment, the tappable contact region comprises a plurality of protrusions extending generally radially inwardly from the inside surface, and a plurality of interstices between the protrusions. According to a yet further aspect, the tappable contact region comprises a porous fiber metal matrix.

According to another embodiment of the present invention, a fastening apparatus adapted for multi-angular insertion is provided. The fastening apparatus comprises a fastener and a fastener receiving member. The fastener comprises an elongate section and an adjoining head section disposed along a fastener axis. The elongate section comprises a first thread and the head section comprises a second thread. The fastener receiving member comprises first and second opposing major surfaces, and an inside surface extending between the first and second major surfaces. The inside surface defines an aperture generally coaxially disposed about an aperture axis. A tappable contact region is disposed on the inside surface. The tappable contact region has a minimum inside diameter that is large enough to permit the elongate section to pass therethrough at an insertion angle defined between the fastener axis and the aperture axis. The tappable contact region is adapted for being tapped by the second thread of the head section to affix the head section to the tappable contact region at the insertion angle.

The present invention also provides a method for affixing a fastener to a fastener receiving member at a desired orientation. A fastener is provided that comprises an elongate section and an adjoining head section disposed along a fastener axis. The elongate section comprises a first thread and the head section comprises a second thread. A fastener receiving member is provided that comprises first and second opposing major surfaces and an inside surface extending between the first and second major surfaces. The inside surface defines an aperture generally coaxially disposed about an aperture axis. A tappable contact region is disposed on the inside surface. An insertion angle, defined between the fastener axis and the aperture axis, is selected as the angle at which the fastener is to be inserted in relation to the fastener receiving member. The elongate section of the fastener is inserted through the aperture until the second thread of the head section contacts the tappable contact region. The fastener is tapped into the receiving member such that the fastener is oriented at the selected insertion angle. This is accomplished by threading the second thread of the head section into the tappable contact region while the fastener is oriented at the selected insertion angle.

According to one aspect of this method, one of the major surfaces of the receiving member is placed against bone material. The first thread of the elongate section of the fastener is threaded into the bone material so as to anchor the fastener to the bone material. This procedure is useful in a number of applications, such as the stabilization and healing of bone fractures. As the first thread of the elongate section is threaded into the bone material, the second thread of the head section eventually contacts the tappable contact region of the fastener receiving member. Further threading of the first thread into the bone material causes the second thread of the head section to be threaded into the tappable contact region of the receiving member.

It is therefore an object of the present invention to provide a plate or other fastener receiving member that enables a threaded fastener to be affixed thereto at a desired angle selected from a range of available angles.

It is another object of the present invention to provide such fastener receiving member with an aperture that does not require a pre-tapped, fixed-position thread structure with which a threaded fastener is to be interfaced.

It is yet another object of the present invention to provide a surgical bone screw/plate system comprising a fastener having a threaded head portion and a fastener receiving member having an aperture lined with a region into which the threaded head portion can be tapped, such that the threaded head portion can be rigidly affixed to the fastener receiving member at an arbitrary angle selected by the user.

Some of the objects of the invention having been stated hereinabove, and which are addressed in whole or in part by the present invention, other objects will become evident as the description proceeds when taken in connection with the accompanying drawings as best described hereinbelow.

BRIEF DESCRIPTION OF THE DRAWINGS

FIG. 2B is a vertical cross-sectional side view of the fastener receiving member illustrated in FIG. 2A taken along cut-away line 2B—2B in FIG. 2A;

DETAILED DESCRIPTION OF THE INVENTION

Figure 1:
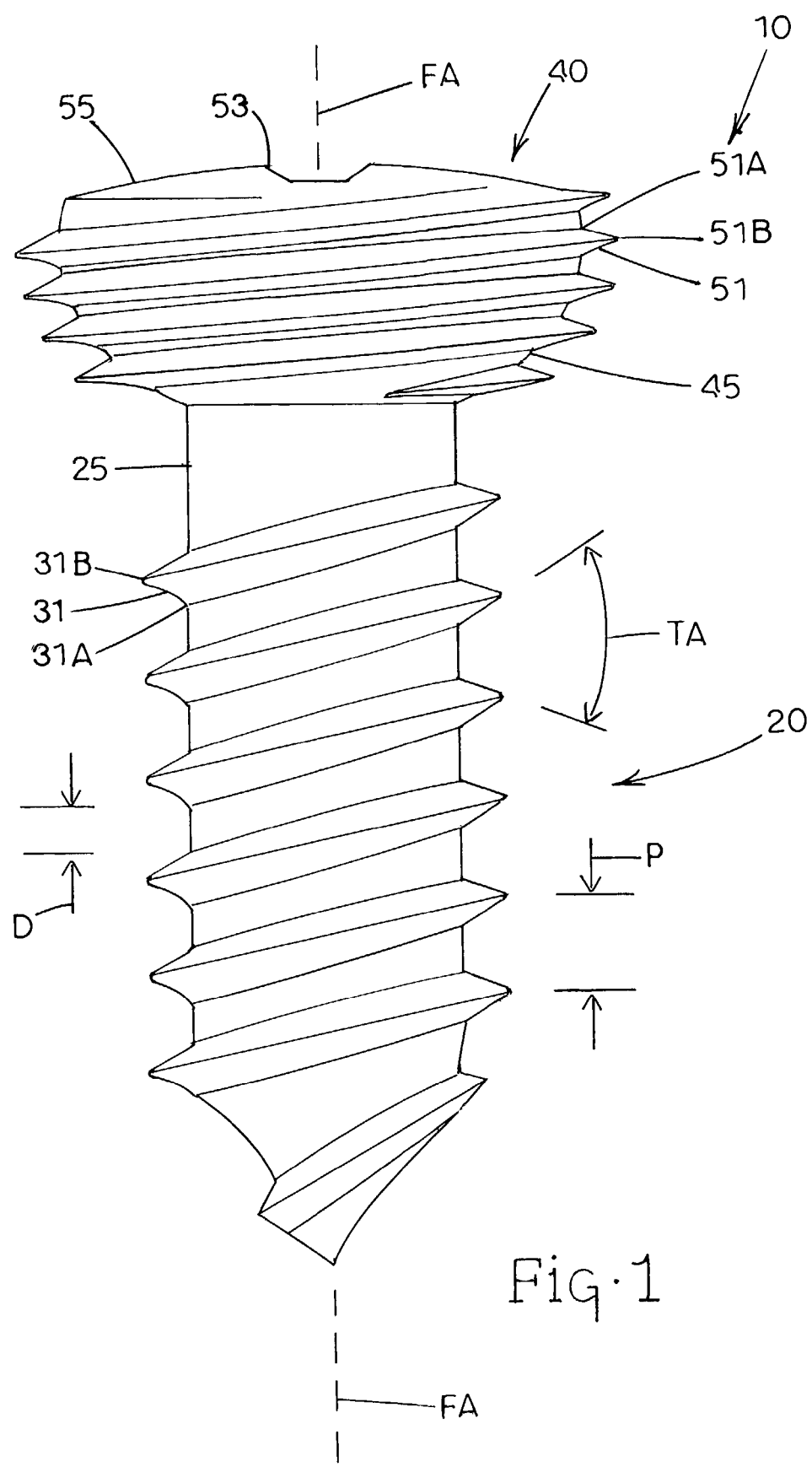
FIG. 1 is an elevation view of a fastener provided in accordance with the present invention.

Referring now to FIG. 1, one example of a threaded-head fastener, generally designated 10, is illustrated in accordance with the present invention. Fastener 10 can be constructed from any material appropriate for withstanding compressive, tensile, torque, or other forces encountered during and after application of fastener 10 to a target site. In the context of orthopaedic surgery, fastener 10 is preferably constructed from a biocompatible metal or metal alloy such as stainless steel, titanium, chromium, or alloys thereof. As is appreciated by persons skilled in the art, fastener 10 could also be constructed from a suitable ceramic material or a polymeric material such as a resorbable polymer, or could be coated with a polymeric film. Fastener 10 comprises an elongate section, generally designated 20, and an adjoining head section, generally designated 40, both of which are generally arranged along a longitudinal fastener axis FA. Elongate section 20 comprises a shaft having a first outer surface 25 coaxially disposed in relation to fastener axis FA. Preferably, first outer surface 25 is cylindrical. Elongate section 20 is machined to form a first thread 31 thereon. First thread 31 has a root 31A adjoining first outer surface 25 from which first thread 31 extends generally radially outwardly to terminate at a crest 31B. First thread 31 winds around first outer surface 25 or a length thereof in a generally helical fashion.

In the illustrated example, first thread 31 has a conical or "V" cross-sectional profile and thus tapers from first outer surface 25 to its crest 31B.

In a preferred implementation of the invention in which fastener 10 is utilized as a bone screw for anchoring to bone material B such as a bone fragment, the illustrated "V" profile of first thread 31 is advantageous in that renders fastener 10 self-tapping. The invention, however, is not limited to any particular design for first thread 31. For instance, the profile of first thread 31 could be rectilinear or square, with its crest 31B being a generally flat surface. Alternatively, the profile of first thread 31 could be trapezoidal (i.e., an "Acme" thread). The degree of sharpness or flatness of crest 31B is not limited, and crest 31B could be rounded. Moreover, the invention is not limited to any particular diameter of first outer surface 25, diameter of crest 31B, thread angle TA between the side walls of adjacent thread passes, or thread pitch P (i.e., the axial distance between the crest portions of adjacent thread passes, or the reciprocal of the number of thread passes per inch). Additionally, first thread 31 could be a multiple-threaded or multi-start design, in which two or more individual threads are cut beside each other. First thread 31 could also constitute one or more single threads formed on different axial sections of shaft. Also, pitch P of first thread 31 could be such that adjacent thread passes are separated from each other by an axial distance D over which only first outer surface 25 of shaft exists. Finally, the "hand" or "sense" associated with the turning of first thread 31 about fastener axis FA may or may not follow the standard right-hand rule.

Figure 4:
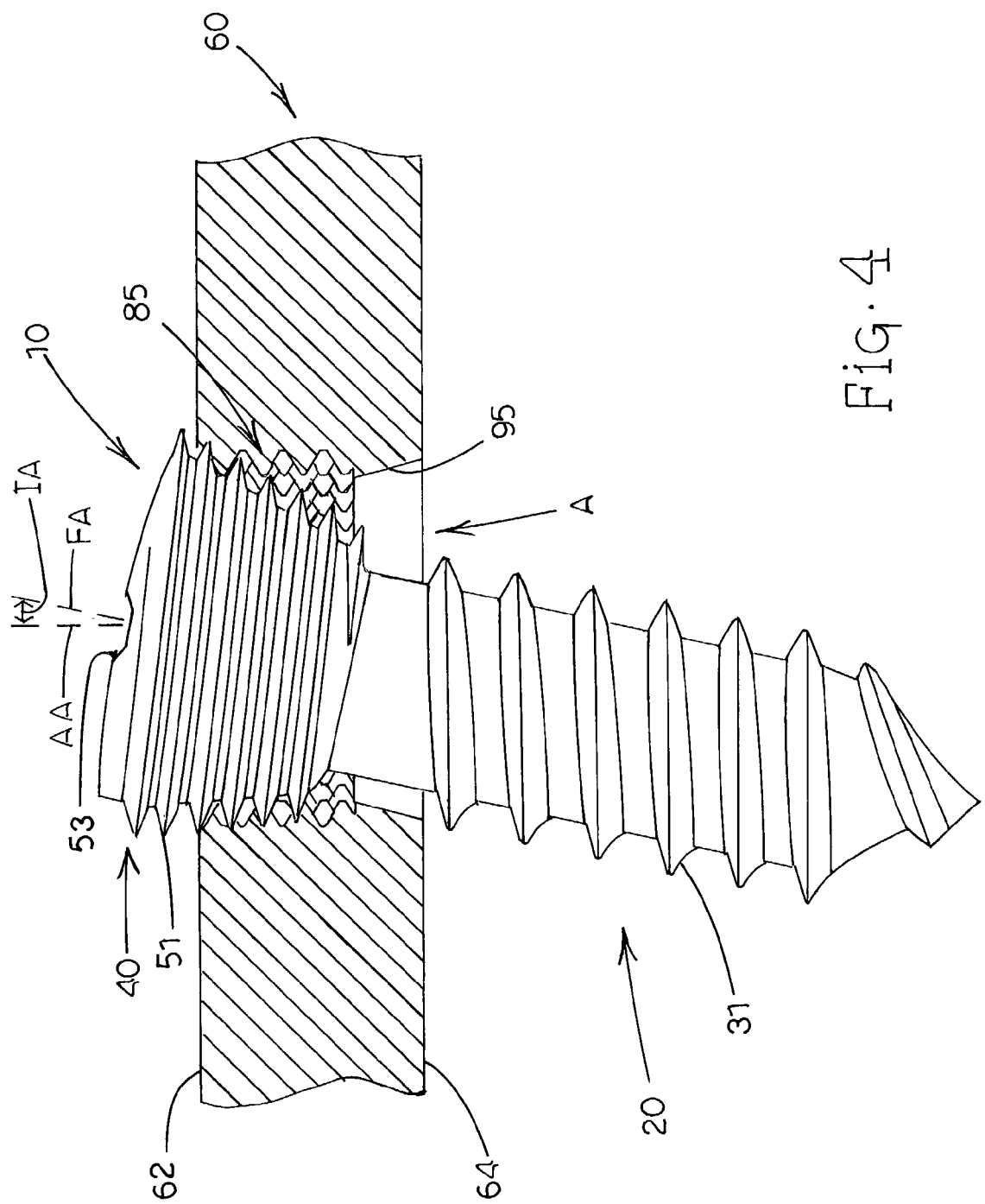
FIG. 4 is a partially cut away and vertical cross-sectional view of a fastener and fastener receiving member according to an alternative embodiment of the present invention.
Figure 5:
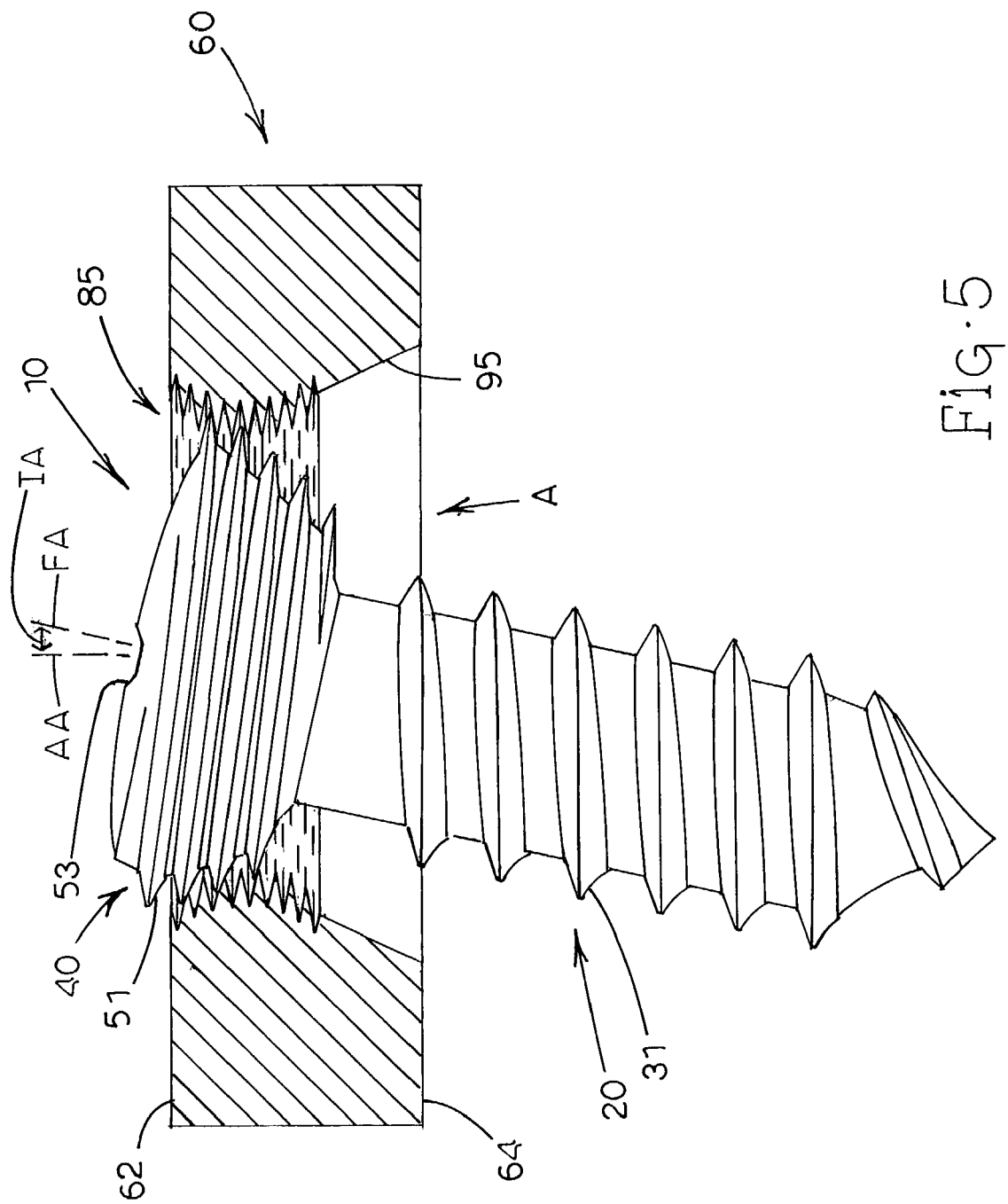
FIG. 5 is a partially cut away and vertical cross-sectional view of a fastener and fastener receiving member according to another alternative embodiment of the present invention.

With continuing reference to FIG. 1, head section 40 comprises a second outer surface 45 coaxially disposed in relation to fastener axis FA. In the example illustrated in FIG. 1, the shape of head section 40, i.e., the cross-sectional profile of second outer surface 45, is substantially hemispherical or parabolic. It will be understood, however, that head section 40 can have other types of rounded shapes, and its profile can be either convex or concave. Moreover, the shape of head section 40 can be substantially frusto-conical as shown in FIGS. 4 and 5. In addition, the shape of head section 40 can be a composite form, such as a converging/diverging or "trumpet-shaped" profile. Head section 40 is machined to form a second thread 51 thereon. Second thread 51, has a root adjoining second outer surface 45 from which second thread 51 extends generally radially outwardly to terminate at a crest 51B. Second thread 51 winds around second outer surface 45 in a generally helical fashion. To facilitate the turning of fastener 10 by the user thereof, a recess 53 is formed in a top surface 55 of head section 40 for the insertion of an appropriate tool such as a screwdriver, key, or wrench. The shape of recess 53 can be a single or cross-shaped slot, a square, a hexagon, a star, or the like.

In the illustrated example, second thread 51 has a conical or "V" profile and thus tapers from second outer surface 45 to crest 51B. The "V" profile of second thread 51 is preferred because it facilitates the self-tapping of head section 40 into a plate or other fastener receiving member 60 (see, e.g., FIGS. 2A and 2B), in accordance with the invention and as described below. However, like first thread 31 of elongate section 20, the invention is not limited to any particular design for second thread 51. Thus, no limitations are made with regard to the profile or shape of first thread 31, the degree of sharpness or flatness of its crest 31B, the outer diameter of any portion of second outer surface 45 or crest 31B (although the average diameter of head section 40 is greater than that of elongate section 20), the thread angle TA, the thread pitch P, the number and locations of the threads constituting second thread 51, or the turning direction of second thread 51 with respect to fastener axis FA.

In an alternative embodiment, elongate section 20 is not threaded, and fastener 10 takes the form of a peg or a pin. This alternative embodiment may be preferred in certain procedures where, for instance, the main object is to prevent tilting of a bone segment, as well as other procedures where there is no concern of fastener 10 pulling out from the bone and hence no need for elongate section 20 to be threaded. In these implementations, head section 40 is threaded, and thus the advantages and benefits of the present invention as described herein apply.

Turning to FIGS. 2A–2D, a fastener receiving member, generally designated 60, is illustrated in accordance with the present invention. In the illustrated example, fastener receiving member 60 is provided in the form of a mounting plate, such as a bone plate for use in orthopaedic surgical procedures. Fastener receiving member 60 can be constructed from any material appropriate for withstanding compressive, tensile, torque, or other forces encountered during and after application of fastener 10 to fastener receiving member 60 at a target site. In the context of orthopaedic surgery, fastener receiving member 60 is preferably constructed from a biocompatible metal or metal alloy such as stainless steel, titanium, cobalt, chromium, tungsten, tantalum, molybdenum, gold, and alloys thereof. Alternatively, fastener receiving member 60 can be constructed from a suitable ceramic or polymeric material. The polymeric material may be reinforced with glass, carbon, or metal fibers.

Fastener receiving member 60 comprises a first major outer surface 62, an opposing second major outer surface 64, and outer lateral edges 66, 67, 68 and 69 at the perimeter. In orthopaedic applications, second outer surface 64 can in some cases be used for contact with bone material B (see FIG. 3), while in other cases actual contact is unnecessary or undesirable. While in the illustrated example first and second outer surfaces 62 and 64 are planar, it will be understood that the cross-section of fastener receiving member 60 or certain portions thereof can have a contoured profile. For instance, in some types of orthopaedic applications, minimum contact between fastener receiving member 60 and the target bone material B might be desired. In such a case, second outer surface 64 or a portion thereof can be convex.

One or more apertures, generally designated A (e.g., apertures $A_1$ and $A_2$ shown in FIGS. 2A and 2B), are formed through the thickness of fastener receiving member 60 for receiving one or more elongate sections 20 of corresponding fasteners 10 therethrough. Each aperture A is defined by an inside surface 81 cut through the thickness of fastener receiving member 60. Each aperture A is generally transversely oriented in relation to first and second outer surfaces 62 and 64, and thus is generally coaxially disposed about a central aperture axis AA (e.g., aperture axis $AA_1$ or $AA_2$ shown in FIG. 2B) directed through the thickness of fastener receiving member 60. The precise number and arrangement of such apertures A can depend on the intended use for fastener receiving member 60. It will be understood, however, that the invention contemplates procedures in which a multi-apertured fastener receiving member 60 is employed in connection with a single fastener 10, with one aperture A of such fastener receiving member 60 being selected by the user for interfacing with the single fastener 10.

Figure 3:
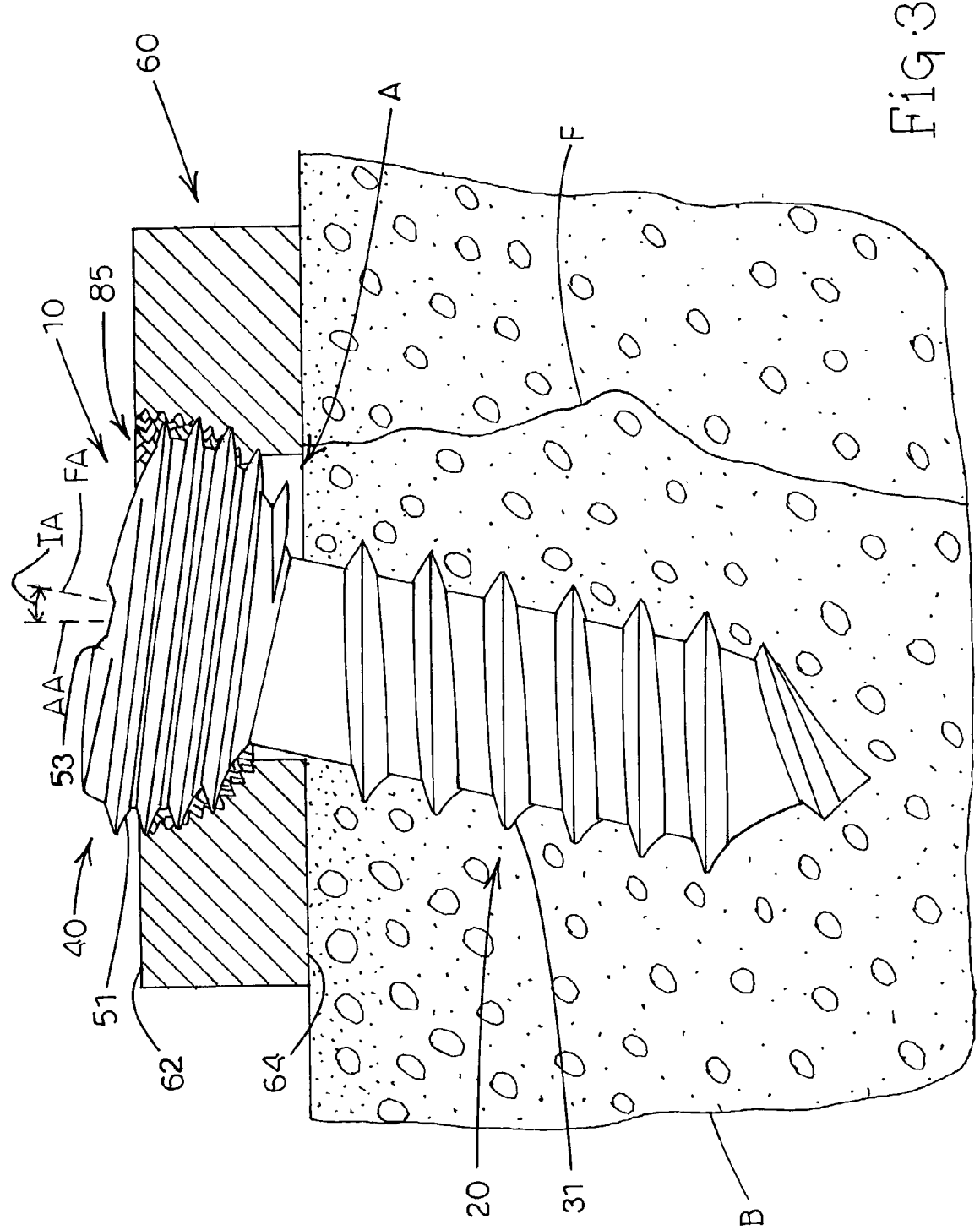
FIG. 3 is a partially cut away and vertical cross-sectional view illustrating an application of the present invention in which the fastener is affixed to the fastener receiving member and anchored to an object such as bone material at a desired insertion angle.

As indicated above, the invention departs from the conventional use of a thread formed on inside surface 81 of aperture A for mating with the thread of a screw head. That is, apertures A of fastener receiving member 60 do not contain a permanent helical thread structure of fixed orientation. Instead, a tappable contact region, generally designated 85, is disposed on each inside surface 81 of fastener receiving member 60. The term "tappable" is used herein to denote that contact region 85 is structured such that it can be tapped by second thread 51 of head section 40 of fastener 10 in response to forceful insertion and rotation of head section 40 into the material of contact region 85. As described below in connection with FIG. 3, this enables the user to manipulate second thread 51 of head section 40 to form, in effect, a custom internal thread in contact region 85 sufficient to maintain fastener 10 at an arbitrary orientation in relation to receiving member 60 selected by the user. In FIG. 3, this orientation is represented by an insertion angle IA, defined between fastener axis FA and aperture axis AA. In accordance with the invention, insertion angle IA can range from 0 to 90 degrees wherein at 0 degrees fastener axis FA coincides with aperture axis AA. Due to the relative positions of aperture A, second outer surface 64 and fastener 10, insertion angle IA in practice will be less than 90 degrees.

Figure 2A:
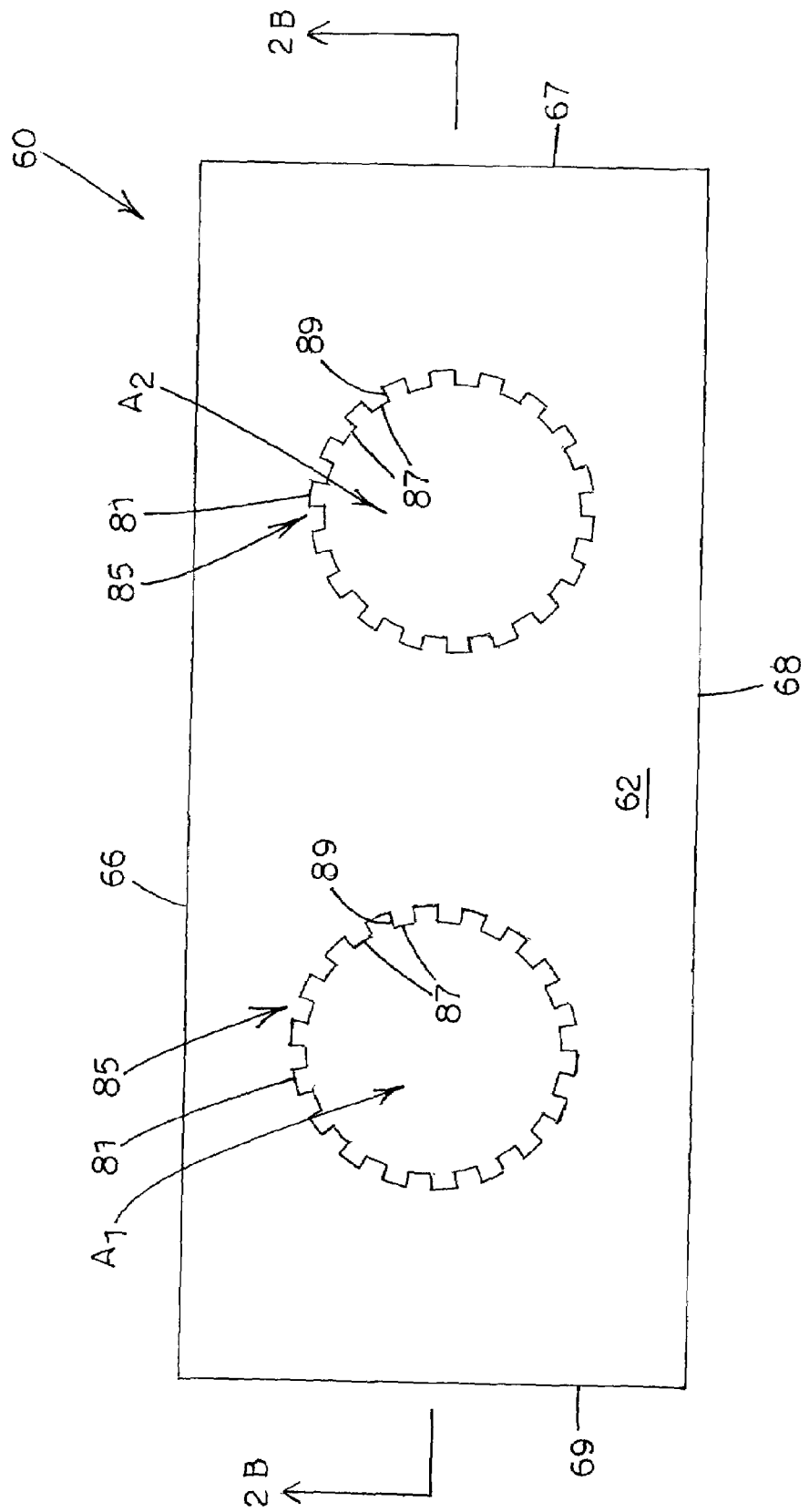
FIG. 2A is a top plan view of a fastener receiving member provided in accordance with the present invention.

In the embodiment illustrated in FIGS. 2A–2D, the tappable property is realized by structuring contact region 85 as a matrix of protrusions 87 and interstices 89 between protrusions 87. Protrusions 87 can be provided in any protruding form, such as pegs, bristles or tines. Protrusions 87 are based on inside surface 81 and extend generally radially inwardly into the open space of apertures A. Protrusions 87 can be formed directly from inside surface 81 and the region of fastener receiving member 60 circumscribing aperture A. Alternatively, as shown in FIG. 2B, protrusions 87 can be formed on a substrate 91 (see FIG. 2B) that is thereafter fitted to inside surface 81 as an insert, such as by press-fitting or binding. The material selected for protrusions 87 can be any material suitable for tapping by fastener 10. Non-limiting examples include stainless steel, titanium, cobalt, chromium, tungsten, tantalum, molybdenum, gold, and alloys thereof, as well as suitable polymers.

It will be noted that the density of protrusions 87 over the area of inside surface 81, and the size of individual protrusions 87, are not limited by the invention, so long as the matrix formed on inside surface 81 renders contact region 85 tappable. Accordingly, the matrix of protrusions 87 can appear as a bristle board or a porous surface. The characteristic cross-sectional dimension of each protrusion 87 (e.g., diameter, width, or the like) can range from approximately 1 micron to approximately 25 mm, although the invention is not limited to this range. The density of protrusions 87 over the area of inside surface 81 from which they protrude can range from approximately 5 to approximately 65%, although the invention is not limited to this range. Protrusions 87 can be formed by any suitable means, such as growing protrusions 87 by material deposition, forming protrusions 87 by coating, welding protrusions 87 to inside surface 81, or forming ridges or grooves and subsequently cutting transversely through the ridges to discretize the ridges into protrusions 87.

Figure 2D:
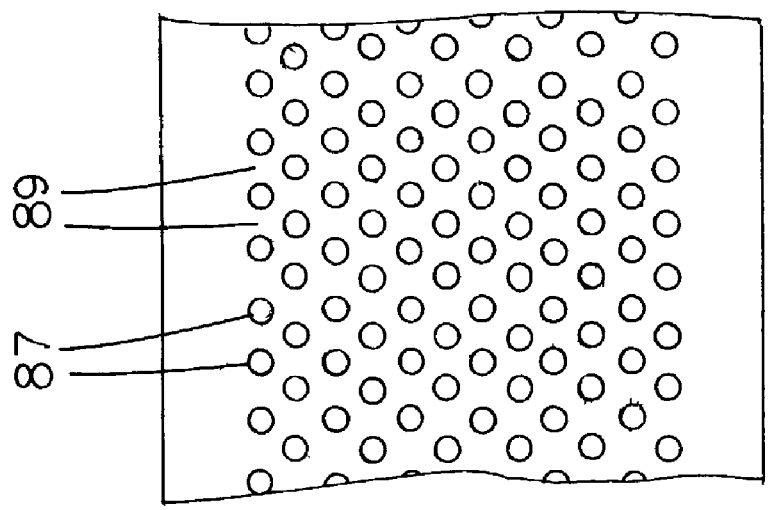
FIG. 2D is a plan view of a section of a contact region in accordance with another embodiment of the present invention.
Figure 2C:
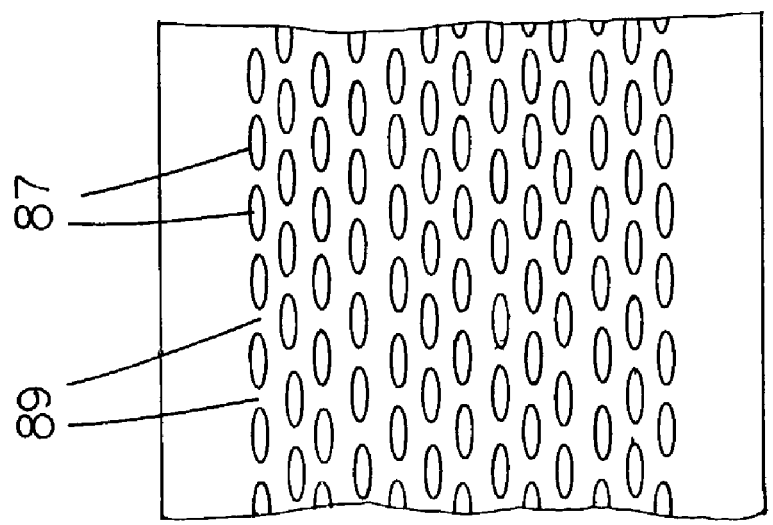
FIG. 2C is a plan view of a section of a contact region provided with the fastener receiving member in accordance with one embodiment of the present invention.

It will be further noted that in the embodiment illustrated in FIGS. 2A and 2B, each protrusion 87 has a generally rectilinear cross-section. The invention, however, encompasses within its scope any cross-section suitable for realizing the tappable property of contact region 85. Hence, as another example, FIG. 2C illustrates an area of contact region 85 in which protrusions 87 are generally elliptical in cross-section. As a further example, FIG. 2D illustrates an area of contact region in which protrusions 87 are generally circular in cross-section. In addition, depending on the density and size of protrusions 87 and the pattern defined by the matrix, protrusions 87 may or may not be deformable as necessary to realize the tappable property of contact region 85.

As seen from the perspective of FIG. 2B, the resultant profile of contact region 85 is illustrated in one embodiment as being rounded to accommodate the rounded profile of head section 40 of fastener 10. The term "resultant" is meant to denote that the profile can be defined by the inside surface 81 itself with each protrusion 87 having a substantially uniform length, or alternatively, the profile can be defined by protrusions 87 of varying lengths. The invention, however, is not limited to any specific profile for contact region 85. In addition, in some embodiments of the invention, contact region 85 is not formed over the entire axial length of inside surface 81. Thus, in FIG. 2B, contact region 85 terminates at a lower section 95 of inside surface 81 (or substrate 91) proximate to second outer surface 64 of fastener receiving member 60.

While the profile of lower section 95 in FIG. 2A is cylindrical, other profiles for lower section 95 are suitable in accordance with the invention. The respective profiles for contact region 85 and any exposed portion of inside surface 81 such as lower section 95 will be dictated in part by the shape of head section 40 of fastener 10, and also by the need to affix fastener 10 over a wide range of available insertion angles IA in relation to receiving member 60 and/or the bone material B or other object in which fastener 10 is to be anchored. Thus, in FIG. 4, a fastener 10 with a conical head section 40 is employed in connection with a receiving member 60 having a contact region 85 of cylindrical profile and a lower section 95 that tapers from second outer surface 64 to contact region 85. As another example, in FIG. 5, a fastener 10 with a rounded head section 40 is employed in connection with a receiving member 60 having a contact region 85 of converging/diverging or trumpet-shaped profile and a lower section 95 of tapering profile. It will be noted for all embodiments that the minimum inside diameter of contact region 85 should be large enough to provide clearance for elongate section 20 and its first thread 31 to pass through aperture A. As one example, the minimum inside diameter can range from approximately 0.5 to approximately 10 mm. In non-orthopaedic applications, the minimum inside diameter can be greater than 10 mm.

Figure 6:
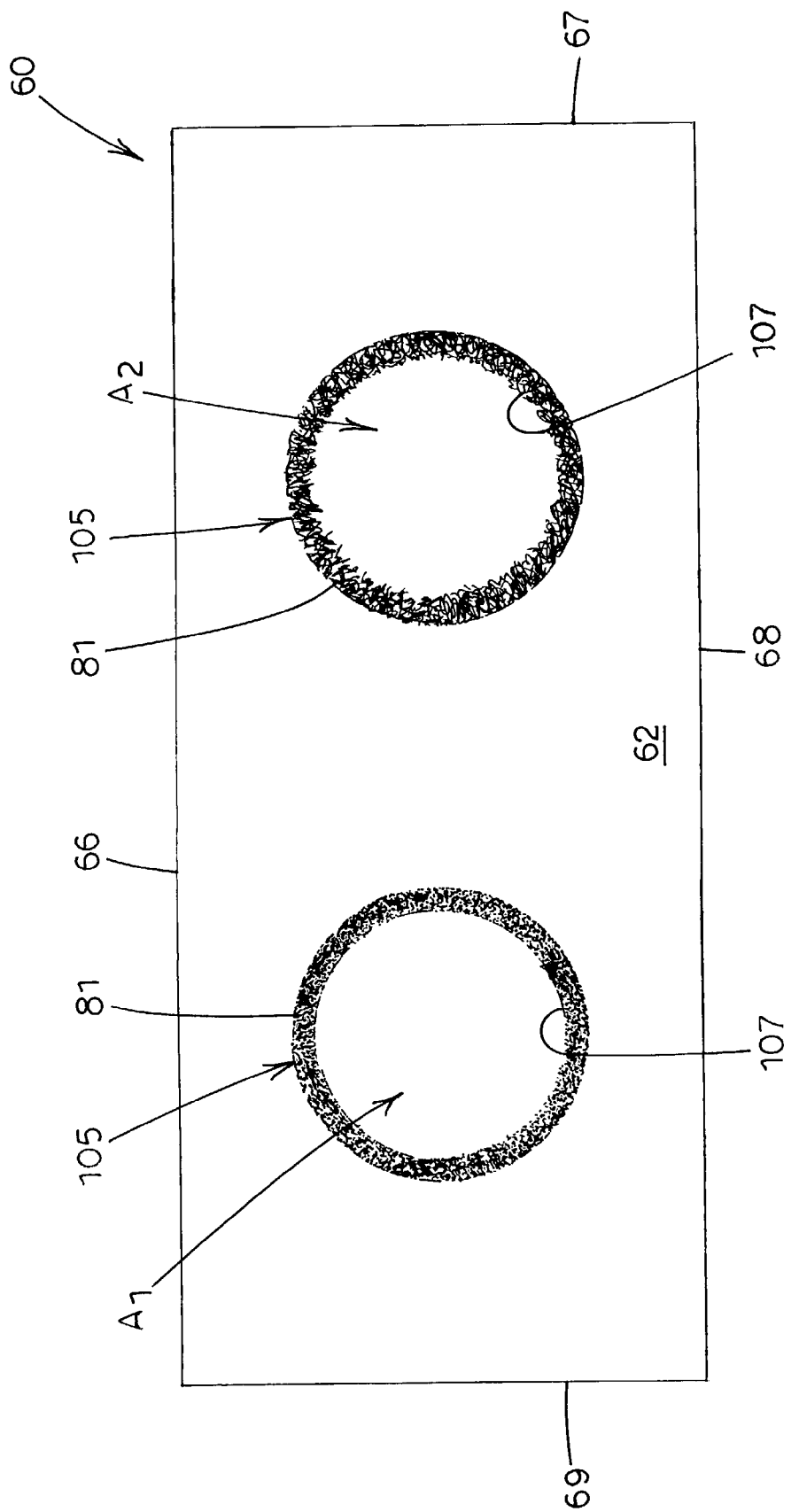
FIG. 6 is a top plan view of a fastener receiving member provided with an alternative contact region provided in accordance with the present invention.
Figure 7:
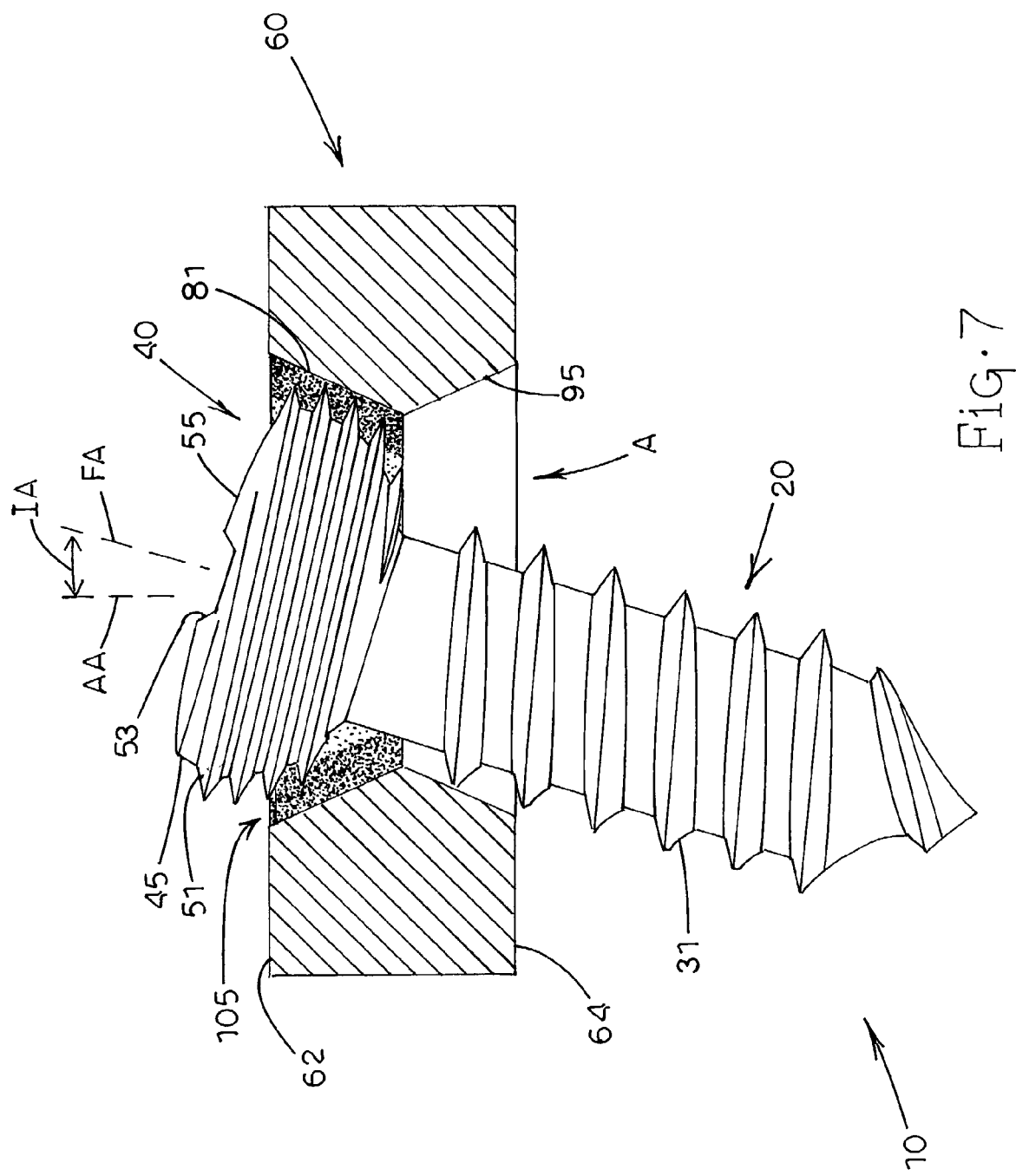
FIG. 7 is a partially cut away and vertical cross-sectional view illustrating the fastener affixed to the fastener receiving member illustrated in FIG. 6.

Referring now to FIGS. 6 and 7, an alternative embodiment of a tappable contact region, generally designated 105, is illustrated. In this embodiment, tappable contact region 105 takes the form of a matrix or mesh of fiber metal 107 that lines inside surface 81 of each aperture A of fastener receiving member 60. As understood by persons skilled in the art, fiber metal consists of a porous or interstitial aggregate of metal or metal alloy wires or fibers. The characteristic cross-sectional dimension of each fiber (e.g., diameter, width, or the like) can range from approximately 1 micron to approximately 25 mm. The porosity of the matrix can range from approximately 40 to approximately 90%. The fibers are often interlocked and kinked in any number of different patterns, and often has the appearance of steel wool. The aggregate can be formed by a variety of techniques. As one example, the fibers can be molded and sintered so as create metallurgical bonds between the fibers and a base surface. The composition of the fibers of contact region 105 can be any biocompatible material that provides contact region 105 with mechanical strength and deformability suitable for being tapped by fastener 10 in accordance with the invention. Non-limiting examples include stainless steel, titanium, cobalt, chromium, tungsten, tantalum, molybdenum, gold, and alloys thereof.

An example of a method for affixing fastener 10 to fastener receiving member 60 will now be described by referring back to FIG. 3, with the understanding that the method can likewise be described in association with the other embodiments illustrated in FIGS. 4–7. It will be further understood that while the present example is given in the context of an orthopaedic surgical procedure, the invention is not so limited. That is, the fastener/receiver system provided by the invention can be applied to any procedure, surgical or non-surgical, in which a threaded fastener is to be tapped into an object and which would benefit by the ability to rigidly orient such fastener at a desired angle in relation to a mounting structure such as fastener receiving member 60.

Turning now to FIG. 3, the surgeon accesses the surgical site of interest, which can be, for example, an internal site at which a bone fracture F is located and requires stabilization to ensure proper healing. The surgeon mounts fastener receiving member 60 against bone material B at a desired location thereof in relation to the bone fracture F. A suitable alignment or mounting tool (not shown) can be employed to retain receiving member 60 in the desired position prior to complete affixation of fastener 10. The surgeon then selects an insertion angle IA, defined hereinabove, as the direction along which fastener 10 is to be inserted through a selected aperture A of receiving member 60 and subsequently driven into a target section of bone material B. If receiving member 60 includes more than one aperture A, the surgeon also selects the specific aperture A to be used. After selecting insertion angle IA and aperture A, the surgeon inserts elongate section 20 of fastener 10 through aperture A until the tip of elongate section 20 contacts bone material B beneath aperture A. In some cases, at this point a hole might be drilled or tapped into bone material B along insertion angle IA to facilitate the initial tapping by fastener 10. The surgeon then inserts an appropriate driving tool (not shown) into recess 53 of head section 40 of fastener 10, and manipulates the driving tool to rotate fastener 10 while forcefully bearing fastener 10 against bone material B. This causes first thread 31 of elongate section 20 to tap into bone material B and anchor fastener 10 to bone material B. As elongate section 20 is driven further through aperture A and into bone material B, head section 40 eventually encounters contact region 85 of aperture A. Due to the intervening presence of contact region 85, the continued driving of fastener 10 into bone material B at this stage causes second thread 51 of head section 40 to tap into contact region 85, thereby rigidly affixing fastener 10 to receiving member 60 at the desired insertion angle IA.

The manner by which head section 40 of fastener 10 is affixed to aperture A of receiving member 60 depends on whether contact region 85 illustrated in FIGS. 2A–3 or contact region 105 illustrated in FIGS. 6 and 7 is provided. In the use of contact region 85, second thread 51 of head section 40 is driven through a series of available interstices 89 (see, e.g., FIGS. 2C and 2D) and between a series of protrusions 87 adjacent to these interstices 89. The driving of second thread 51 causes this series of protrusions 87 to contact second thread 51 and maintain fastener 10 at the desired insertion angle IA. As described hereinabove, protrusions 87 contacting second thread 51 may or may not deform or otherwise move in response to the driving of second thread 51 into contact region 85. On the other hand, in the use of contact region 105, the metal fibers will deflect in response to the driving of second thread 51 and envelop second thread 51. The mechanical strength of the fibers contacting or proximate to second thread 51 is sufficient to maintain fastener 10 at the desired insertion angle IA. Some of the fibers may be cut in response to the driving of second thread 51 into contact region 105. With the use of either contact region 85 or contact region 105, the driving of second thread 51 through aperture A in effect forms a custom internal thread in contact region 85 or 105 that is complimentary to the orientation and structure of second thread 51 and turns in relation to fastener axis FA.

Depending on the nature of the procedure being executed, the surgeon can affix additional fasteners 10 to additional apertures A of receiving member 60, either at the same insertion angle IA as the illustrated fastener 10 or at different angles. It will be noted that, depending on the number of fasteners 10 utilized and how far each is threaded into its corresponding aperture A, the mechanical strength of the interface between each corresponding second thread 51 and contact region 85 or 105 can be made sufficient to cause compression of receiving member 60 against bone material B if desired by the surgeon.

As an alternative to the embodiments specifically illustrated in FIGS. 1–7, the interface between second thread 51 of head section 40 and contact region 85 or 105 of aperture A could be reversed. That is, head section 40 of fastener 10 could be provided with contact region 85 or 105, and aperture A of fastener receiving member 60 could be provided with second thread 51. This alternative embodiment likewise enables fastener 10 to be rigidly secured non-coaxially to aperture A.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A surgical plate adapted for fixation with a bone screw, comprising first and second opposing major surfaces, an inside surface extending between the first and second major surfaces and defining an aperture generally coaxially disposed about an aperture axis, and a non-rotatable, non-threaded tappable contact region disposed on the inside surface of the aperture, the tappable contact region having an inside diameter large enough to permit a bone screw to pass therethrough at a variable insertion angle defined between the longitudinal axis of the bone screw and the aperture axis, and the tappable contact region is formed so as to allow for being tapped by an external thread of the bone screw to rigidly affix the bone screw to the tappable contact region at a selected one of a plurality of different insertion angles that can be selectively formed between the axis of the bone screw and the aperture axis.

2. The surgical plate according to claim 1 wherein the first and second major surfaces are disposed generally transversely in relation to the aperture axis.

3. The surgical plate according to claim 1 comprising a plurality of inside surfaces, each inside surface defining a respective aperture generally coaxially disposed about a respective aperture axis, and a plurality of tappable contact regions respectively disposed on the inside surfaces.

4. The surgical plate according to claim 1 wherein the tappable contact region has a substantially cylindrical vertical profile.

5. The surgical plate according to claim 1 wherein the tappable contact region has a rounded vertical profile.

6. The surgical plate according to claim 1 wherein the tappable contact region has a substantially hemispherical vertical profile.

7. The surgical plate according to claim 1 wherein the tappable contact region has a substantially frusto-conical vertical profile.

8. The surgical plate according to claim 1 wherein the tappable contact region has a converging/diverging vertical profile.

9. The surgical plate according to claim 1 wherein the tappable contact region is formed in the inside surface of the aperture.

10. The surgical plate according to claim 1 wherein the tappable contact region comprises an insert fitted to the inside surface.

11. The surgical plate according to claim 1 wherein the tappable contact region comprises a plurality of protrusions extending generally radially inwardly from the inside surface and a plurality of interstices between the protrusions.

12. The surgical plate according to claim 11 wherein the protrusions are constructed from a metal-containing material.

13. The surgical plate according to claim 11 wherein the protrusions are constructed from a polymeric material.

14. The surgical plate according to claim 11 wherein the protrusions have substantially polygonal cross-sections.

15. The surgical plate according to claim 11 wherein the protrusions have substantially rounded cross-sections.

16. The surgical plate according to claim 1 wherein the tappable contact region comprises a porous fiber metal matrix.

17. The surgical plate according to claim 16 wherein the fiber metal matrix comprises a plurality of titanium-containing fibers.

18. The surgical plate according to claim 1 wherein the minimum inside diameter of the tappable contact region ranges from approximately 0.5 to approximately 10 mm.

19. The surgical plate according to claim 1 wherein the minimum inside diameter of the tappable contact region is greater than 10 mm.

20. The surgical plate according to claim 1 wherein the insertion angle ranges from approximately 0 to approximately 90 degrees.

21. A fastening apparatus adapted for multi-angular insertion, comprising:
  (a) a fastener comprising an elongate section and an adjoining head section disposed along a fastener axis, the head section comprising a thread; and
  (b) a fastener receiving member comprising first and second opposing major surfaces, an inside surface extending between the first and second major surfaces and defining an aperture generally coaxially disposed about an aperture axis, and a non-rotatable tappable contact region disposed on the inside surface of the aperture, the tappable contact region having an inside diameter large enough to permit the elongate section of the fastener to pass therethrough at a variable insertion angle defined between the fastener axis and the aperture axis, and the tappable contact region is formed so as to allow for being tapped by the thread of the head section to rigidly affix the head section to the tappable contact region at a selected one of a plurality of different angles that can be selectively formed between the axis of the fastener and the aperture axis.

22. The apparatus according to claim 21 wherein the fastener is a surgical bone screw.

23. The apparatus according to claim 21 wherein the elongate section comprises a thread.

24. The apparatus according to claim 23 wherein the elongate section comprises a first outer surface, and the thread of the elongate section extends along a length of the first outer surface in generally helical relation to the fastener axis.

25. The apparatus according to claim 24 wherein the head section comprises a second outer surface, and the thread of the head section extends along a length of the second outer surface in generally helical relation to the fastener axis.

26. The apparatus according to claim 23 wherein the head section has a rounded vertical profile.

27. The apparatus according to claim 23 wherein the head section has a substantially hemispherical vertical profile.

28. The apparatus according to claim 23 wherein the head section has a substantially frusto-conical vertical profile.

29. The apparatus according to claim 23 wherein the head section has a converging/diverging vertical profile.

30. The apparatus according to claim 21 wherein the first and second major surfaces of the fastener receiving member define a surgical plate.

31. The apparatus according to claim 21 wherein the tappable contact region is formed in the inside surface of the fastener receiving member.

32. The apparatus according to claim 21 wherein the tappable contact region comprises an insert fitted to the inside surface.

33. The apparatus according to claim 21 wherein the tappable contact region comprises a plurality of protrusions extending generally radially inwardly from the inside surface and a plurality of interstices between the protrusions.

34. The apparatus according to claim 33 wherein the protrusions are constructed from a metal-containing material.

35. The apparatus according to claim 33 wherein the protrusions comprise a polymeric material.

36. The apparatus according to claim 21 wherein the tappable contact region comprises a porous fiber metal matrix.

37. The apparatus according to claim 36 wherein the fiber metal matrix comprises a plurality of titanium-containing fibers.

38. The apparatus according to claim 21 wherein the insertion angle ranges from approximately 0 to approximately 90 degrees.

39. A method for affixing a fastener to a fastener receiving member at a desired orientation, comprising the steps of:
  (a) providing a fastener comprising an elongate section and an adjoining head section disposed along a fastener axis, the head section comprising a thread;
  (b) providing a fastener receiving member comprising first and second opposing major surfaces, an inside surface extending between the first and second major surfaces and defining an aperture generally coaxially disposed about an aperture axis, and a non-rotatable tappable contact region disposed on the inside surface of the aperture, the tappable contact region having an inside diameter large enough to permit the elongate section of the fastener to pass therethrough at a variable insertion angle defined between the fastener axis and the aperture axis, and the contact region is formed so as to allow for being tapped by the thread of the head section to rigidly affix the head section to the tappable contact region at a selected one of a plurality of different angles that can be selectively formed between the axis of the fastener and the apertur axis;
  (c) selecting one of the plurality of different insertion angles at which the fastener is to be inserted in relation to the fastener receiving member;

(d) inserting the elongate section through the aperture until the thread of the head section contacts the non-rotatable tappable contact region; and (e) tapping the fastener into the receiving member such that the fastener is rigidly oriented at the selected insertion angle by threading the thread of the head section into the non-rotatable tappable contact region while the fastener is oriented at the selected insertion angle.

40. The method according to claim 39 comprising the steps of placing one of the major surfaces of the receiving member against bone material, and inserting the elongate section of the fastener into the bone material.

41. The method according to claim 40 wherein the elongate section is threaded, and inserting the elongate section into the bone material comprises threading the elongate section into the bone material.

42. The method according to claim 41 wherein threading of the elongate section further into the bone material causes threading of the thread of the head section into the tappable contact region of the receiving member.

43. The method according to claim 39 wherein the tappable contact region comprises a plurality of protrusions extending generally radially inwardly from the inside surface and a plurality of interstices between the protrusions, and tapping the fastener comprises driving the thread of the head section through a series of the interstices and into contact with a series of the protrusions.

44. The method according to claim 43 wherein driving the thread of the head section into contact with the series of protrusions deforms at least some of the protrusions.

45. The method according to claim 39 wherein the tappable contact region comprises a porous fiber metal matrix, and the step of tapping the fastener comprises driving the thread of the head section into the matrix to create a screw path in the matrix.

46. The method according to claim 45 wherein driving the thread of the head section into the matrix cut, deforms, or deflects fibers of the matrix.

47. A surgical plate adapted for fixation with a bone screw, comprising first and second opposing major surfaces, an inside surface extending between the first and second major surfaces and defining an aperture generally coaxially disposed about an aperture axis, and a non-threaded tappable contact region disposed on the inside surface, wherein the tappable contact region has a minimum inside diameter large enough to permit a bone screw to pass therethrough at an insertion angle defined between a longitudinal axis of the bone screw and the aperture axis, and the tappable contact region is adapted for being tapped by an external thread of the bone screw to affix the bone screw to the tappable contact region at the insertion angle and wherein the tappable contact region comprises a plurality of protrusions extending generally radially inwardly from the inside surface and a plurality of interstices between the protrusions.

48. The surgical plate according to claim 47 wherein the protrusions are constructed from a metal-containing material.

49. The surgical plate according to claim 47 wherein the protrusions are constructed from a polymeric material.

50. The surgical plate according to claim 47 wherein the protrusions have substantially polygonal cross-sections.

51. The surgical plate according to claim 47 wherein the protrusions have substantially rounded cross-sections.

52. The surgical plate according to claim 47 wherein the tappable contact region comprises a porous fiber metal matrix.

53. The surgical plate according to claim 52 wherein the fiber metal matrix comprises a plurality of titanium-containing fibers.

54. A fastening apparatus adapted for multi-angular insertion, comprising:

(a) a fastener comprising an elongate section and an adjoining head section disposed along a fastener axis, the head section comprising a thread, said fastener comprising a surgical bone screw; and (b) a fastener receiving member comprising first and second opposing major surfaces, an inside surface extending between the first and second major surfaces and defining an aperture generally coaxially disposed about an aperture axis, and a tappable contact region disposed on the inside surface, wherein the tappable contact region has a minimum inside diameter large enough to permit the elongate section to pass therethrough at an insertion angle defined between the fastener axis and the aperture axis, and the tappable contact region is adapted for being tapped by the thread of the head section to affix the head section to the tappable contact region at the insertion angle.

55. The apparatus according to claim 54 wherein the elongate section comprises a thread.

56. The apparatus according to claim 55 wherein the elongate section comprises a first outer surface, and the thread of the elongate section extends along a length of the first outer surface in generally helical relation to the fastener axis.

57. The apparatus according to claim 56 wherein the head section comprises a second outer surface, and the thread of the head section extends along a length of the second outer surface in generally helical relation to the fastener axis.

58. The apparatus according to claim 54 wherein the head section has a rounded vertical profile.

59. The apparatus according to claim 54 wherein the head section has a substantially hemispherical vertical profile.

60. The apparatus according to claim 54 wherein the head section has a substantially frusto-conical vertical profile.

61. The apparatus according to claim 54 wherein the head section has a converging/diverging vertical profile.

62. The apparatus according to claim 54 wherein the first and second major surfaces of the fastener receiving member define a surgical plate.

63. The apparatus according to claim 54 wherein the tappable contact region is formed in the inside surface of the fastener receiving member.

64. The apparatus according to claim 54 wherein the tappable contact region comprises an insert fitted to the inside surface.

65. The apparatus according to claim 54 wherein the tappable contact region comprises a plurality of protrusions extending generally radially inwardly from the inside surface and a plurality of interstices between the protrusions.

66. The apparatus according to claim 65 wherein the protrusions are constructed from a metal-containing material.

67. The apparatus according to claim 65 wherein the protrusions comprise a polymeric material.

68. The apparatus according to claim 54 wherein the tappable contact region comprises a porous fiber metal matrix.

69. The apparatus according to claim 68 wherein the fiber metal matrix comprises a plurality of titanium-containing fibers.

70. The apparatus according to claim 54 wherein the insertion angle ranges from approximately 0 to approximately 90 degrees.

71. A method for affixing a fastener to a fastener receiving member at a desired orientation, comprising the steps of:
- (a) providing a fastener comprising a threaded elongate section and an adjoining head section disposed along a fastener axis, the head section comprising a thread;
- (b) providing a fastener receiving member comprising first and second opposing major surfaces, an inside surface extending between the first and second major surfaces and defining an aperture generally coaxially disposed about an aperture axis, and a tappable contact region disposed on the inside surface;
- (c) selecting an insertion angle at which the fastener is to be inserted in relation to the fastener receiving member, wherein the insertion angle is defined between the fastener axis and the aperture axis;
- (d) inserting the elongate section through the aperture until the thread of the head section contacts the tappable contact region;
- (e) tapping the fastener into the receiving member such that the fastener is oriented at the selected insertion angle by threading the thread of the head section into the tappable contact region while the fastener is oriented at the selected insertion angle; and
- (f) comprising the step of placing one of the major surfaces of the receiving member against bone material, and inserting the elongate section of the fastener into the bone material by threading the elongate section into the bone material.

72. The method according to claim 71 wherein threading of the elongate section further into the bone material causes threading of the thread of the head section into the tappable contact region of the receiving member.

73. The method according to claim 71 wherein the tappable contact region comprises a plurality of protrusions extending generally radially inwardly from the inside surface and a plurality of interstices between the protrusions, and tapping the fastener comprises driving the thread of the head section through a series of the interstices and into contact with a series of the protrusions.

74. The method according to claim 73 wherein driving the thread of the head section into contact with the series of protrusions deforms at least some of the protrusions.

75. The method according to claim 71 wherein the tappable contact region comprises a porous fiber metal matrix, and the step of tapping the fastener comprises driving the thread of the head section into the matrix to create a screw path in the matrix.

76. The method according to claim 75 wherein driving the thread of the head section into the matrix cut, deforms, or deflects fibers of the matrix.

* * * * *

(12) INTER PARTES REVIEW CERTIFICATE (109th)
United States Patent  (10) Number: US 6,955,677 K1
Dahners  (45) Certificate Issued: Jan. 12, 2016

(54) MULTI-ANGULAR FASTENING APPARATUS AND METHOD FOR SURGICAL BONE SCREW/PLATE SYSTEMS

(75) Inventor: Laurence E. Dahners

(73) Assignee: THE UNIVERSITY OF NORTH CAROLINA AT CHAPEL HILL

Trial Number:

IPR2014-00626 filed Apr. 14, 2014

Petitioner: Wright Medical Technology, Inc.

Patent Owner: The University of North Carolina at Chapel Hill

Inter Partes Review Certificate for:

Patent No.: 6,955,677
Issued: Oct. 18, 2005
Appl. No.: 10/271,635
Filed: Oct. 15, 2002

The results of IPR2014-00626 are reflected in this inter partes review certificate under 35 U.S.C. 318(b).

INTER PARTES REVIEW CERTIFICATE
U.S. Patent 6,955,677 K1
Trial No. IPR2014-00626
Certificate Issued Jan. 12, 2016

AS A RESULT OF THE INTER PARTES REVIEW PROCEEDING, IT HAS BEEN DETERMINED THAT:

Claims 1-4, 9, 18, 21-25, 28, 30, 31, 39-42, 54-57, 60, 62, 63, 71 and 72 are disclaimed.

\* \* \* \* \*